(12) United States Patent
King et al.

(10) Patent No.: US 7,379,577 B2
(45) Date of Patent: May 27, 2008

(54) METHOD AND APPARATUS FOR PARTICLE MEASUREMENT EMPLOYING OPTICAL IMAGING

(75) Inventors: Frederick David King, Richmond (CA); Serge Emile LeBlanc, Ottawa (CA)

(73) Assignee: Brightwell Technologies, Stittsville (CA)

( * ) Notice: Subject to any disclaimer, the term of this patent is extended or adjusted under 35 U.S.C. 154(b) by 755 days.

(21) Appl. No.: 10/985,111

(22) Filed: Nov. 10, 2004

(65) Prior Publication Data

US 2005/0099626 A1 May 12, 2005

Related U.S. Application Data

(60) Provisional application No. 60/518,309, filed on Nov. 10, 2003.

(51) Int. Cl.
*G06K 9/00* (2006.01)
(52) U.S. Cl. ........................ 382/133; 356/335
(58) Field of Classification Search ................ 382/100, 382/128, 133, 134; 356/335, 336, 337, 338
See application file for complete search history.

(56) References Cited

U.S. PATENT DOCUMENTS

| | | | |
|---|---|---|---|
| 5,438,408 A | 8/1995 | Weichert et al. ............ 356/336 |
| 6,061,130 A | 5/2000 | Plate et al. .................. 356/335 |
| 7,064,826 B2* | 6/2006 | Rabinski et al. ............ 356/335 |
| 2002/0159047 A1* | 10/2002 | Dubois ....................... 356/28.5 |
| 2004/0008867 A1* | 1/2004 | Fein et al. ................... 382/100 |

* cited by examiner

Primary Examiner—Andrew W. Johns
(74) Attorney, Agent, or Firm—Teitelbaum & MacLean; Neil Teitelbaum; Doug MacLean

(57) ABSTRACT

A system and method for measuring small particles suspended in a fluid are disclosed. The system employs optical imaging using diffraction enlargement. A sample of small particles illuminated by a light source is imaged onto a pixel array of detector elements using an imaging optical system having a reduced magnification not sufficient for forming a large enough image of a smallest particle of interest. A low-aperture imaging optics with NA<0.05 is used to add diffraction enlargement to the image corresponding to at least 5 pixels to enable accurate measurement of images of smallest particles of interest, and to increase an optical sampling volume. Suitably programmed processor is used for determining at least a pixel count for each of the diffraction-enlarged images, and for generating a number, size or distribution of particles accounting for pre-determined diffraction enlargement of particle images of different sizes. The method enables analysis of large samples of small particles in one measurement.

15 Claims, 2 Drawing Sheets

METHOD AND APPARATUS FOR PARTICLE MEASUREMENT EMPLOYING OPTICAL IMAGING

CROSS-REFERENCE TO RELATED APPLICATIONS

This application claims priority of U.S. Provisional Patent Application No: 60/518,309 filed Nov. 10, 2003, entitled "Method And Apparatus For Particle Measurement Employing Optical Imaging", which is incorporated herein by reference for all purposes.

FIELD OF THE INVENTION

The present invention relates to measuring a characteristic of a population of small particles within a volume of a sample of a fluid by optical imaging.

BACKGROUND OF THE INVENTION

Many prior art systems exist for detecting the presence of particles or size of particles in a fluid, such as a supply of potable water. For example, U.S. Pat. No. 5,438,408 entitled Measuring Device and Method for the Determination of Particle Size Distributions by Scattered Light Measurements discloses the use of a charge coupled device (CCD) camera. U.S. Pat. No. 6,061,130 entitled Apparatus for Determining the Particle Size Distribution of a Mixture discloses an apparatus that includes a CCD matrix. By identifying particles by predetermined parameters, such as diameter or cross-sectional area, such systems can ascertain the presence or absence of unwanted harmful bacteria in a water sample which are known to be within a predetermined range of diameters.

Some of these systems have also been known to be useful in analyzing other fluids such as blood and blood products. Typically, identifying particle populations in accordance with some parameter, for instance particle size or particle cross-section, allows a parameter distribution to be ascertained. In a water supply the goal may be to determine the number of particles of various sizes that are present in a representative sample.

Detection systems most often employ the use of computers or powerful processor-based systems coupled to one or more CCD or pixel arrays of detecting elements, which detect the presence of one or more particles projected upon a portion of the array of charge coupled elements. Often thousands of frames of information are collected. Within a single frame more than a single particle may be detected; therefore, the software is programmed to find clusters of pixels, indicating the presence of a particle, and to determine a number of pixels, or a pixel total, for the cluster. Some software can determine instances where portions of particles overlap and determine the size of each particle.

In each successive frame, images of the particles contained within an optical sampling volume are projected onto the pixel array by a magnification system. These images of the particles are randomly distributed on the array depending on the positions of the particles in the sampling volume. In order to produce the parameter distribution information, the parameter value corresponding to each pixel total must be determined. When the number of pixels is large, a simple scaling factor, which depends only on the pixel size and the magnification, gives accurate results. However when the number of pixels is small, that is, when only very few detectors sense the presence of at least a portion of a particle, this scaling factor becomes increasingly uncertain and depends more strongly on the image location and on a detector sensitivity threshold.

Image location error results from the fact that the pixel total measured for a particular value of a particle image depends on the location of the image with respect to the pixel grid. This can be understood more clearly by way of example considering a particle which image has a cross-sectional area corresponding to exactly one array element. Such an image can overlap, either completely or partially, from one to four array elements, and therefore can potentially trigger from one to four array elements, or pixels, depending on the image position with respect to the detector array and the sensitivity threshold setting of the detector elements.

Whether a partially exposed element of the detector array will trigger a pixel count depends on the detector sensitivity threshold, which contributes to uncertainty of the relation between a particle size and a pixel total count of its image. This uncertainty, which decreases with increasing the pixel total count, is hereafter referred to in this specification as a pixelation error. A minimum number of 9 pixels are normally considered to be required to achieve approximately 30% accuracy in a single image measurement. In applications, and depending on a data processing technique used, this minimum pixel count threshold $N_{min}$ of reliable image detection can be either larger or less than 9.

A method of at least partially obviating negative effects of the pixelation errors on obtaining a parameter distribution from digital images of a sample of particles was disclosed in a U.S. patent application Ser. No. 10/653,133 filed Sep. 3, 2003 by a same inventor, which is incorporated herein by reference. The method involves post-processing of the measured statistical data containing pixel count per image using pre-determined probability coefficients relating a pixel total count to a particle size, which can be obtained for example by measuring a statistically large sample of particles of same diameter and analyzing statistical distribution of the pixel count per image. Using this method, reliable statistical information about particle size distribution in a sample containing statistically significant number of small particles can be obtained using a small number of pixels per image without significantly suffering from the effects of the pixelation error normally associated with using a small number of pixels.

An ability of the prior art systems to measure large samples of small particles is however limited by the used magnification system; regardless of a particular value of the minimum pixel count per image adopted for the system, as the particles of interest become smaller, a proportionally larger magnification factor is normally required to reliably detect smaller particles, leading to an undesirable reduction of a sample size that can be analyzed in one measurement.

For in-line operation or, in applications where a large number of samples must be analyzed, it is desirable that measurements be made in the shortest possible time. For example it would be desirable to analyze a sample in several minutes and not in several hours. Furthermore, it is desirable that a single measurement at a single magnification provides information, i.e. the number of particles in each of a specified range of equivalent diameters for the particles having the largest possible range of sizes.

To ensure that that the pixelation error is small, a sufficiently high magnification may be selected so that the images of the smallest particles occupy a sufficient number of pixels, no less than a fixed minimum pixel total $N_{min}$. In magnification systems used for imaging in conventional microscopy, the optics is designed to provide a magnified image, which has minimum distortion and closely resembles the particle under examination. In such systems, the optical sampling volume over which non-distorted images may be obtained is a product of a field of view and a depth of focus of the optics used; at sufficient magnification it is very small, and become smaller as the magnification is increased. Typically, a system with 15 times magnification used to image 2 micron particles would have a depth of focus of approximately 2.5 microns and a field of view on the pixel array of approximately 0.5×0.5 mm. The resultant small optical sampling volume severely limits the number of particles in a flowing stream, which may be in-focus for measurement at a given time. By way of example: the time required to analyze a typical sample of 1 cc, using a magnification such that a 2.5 micron particle occupies two hundred 7.5×7.5 micron pixels, is approximately 5 hours. Furthermore as magnification is increased, the size of the largest particle, which may be imaged without incurring a significant probability that its image will overlap with the edge of the pixel array, is reduced; for the magnification value used in the example, this upper limit is approximately 50 microns. As a result, conventional microscopy has not been commercially used heretofore to make measurements on particle populations in flowing streams.

For maximum measurement speed and maximum parameter measurement range it is desirable that largest sample volumes could be measured in a single measurement using a smallest possible magnification factor that provides sufficient number of pixels in the image of the smallest particle to be included in the characterization of the population.

It is an object of this invention, to provide a relatively fast and inexpensive imaging system whereby a small magnification factor can be used to image a small particle in a large sample volume.

SUMMARY OF THE INVENTION

In accordance with the invention, a system for measuring small particles suspended in a fluid is provided comprising: a pixel array of detector elements for simultaneously detecting one or more images of the particles formed thereupon; an imaging system for forming the images of the particles on the pixel array, said imaging system comprising imaging optics for causing a diffraction enlargement of each of the images by at least $n_d$ pixels each thereby providing diffraction-enlarged images, said at least $n_d$ pixels in operation capturing a diffraction-induced component of each diffraction-enlarged image, wherein $n_d$ is equal to 5; and, suitably programmed processing means for determining at least a pixel count for each of the diffraction-enlarged images, and for generating a number, size or distribution of particles, in dependence upon the diffraction-enlarged images captured by said imaging system.

In accordance with another aspect of this invention, the imaging optics has a numerical aperture NA selected to provide the diffraction enlargement by at least $n_d$ pixels of the images of small particles having a minimum diameter $d_{min}$ less than 3 μm for obtaining the images with a predetermined minimum pixel count per image $n_{min}$ for image detection, wherein $n_d$ is greater than $3 \times n_{min}$.

In accordance with another aspect of this invention, the imaging optics has a linear magnification factor m less than $3 \times p/d_{min}$, wherein p is a pixel size of the pixel array of detector elements.

In accordance with another aspect of this invention, the system has processing means adapted for calculating a particle size for a plurality of particles in a sample in the presence of diffraction enlargement, wherein the processing means includes memory having a plurality of scaling coefficients stored therein, said scaling coefficients relating the particle size to a pixel count.

In accordance with another aspect of this invention, the system for measuring small particles having a diameter $d_{min}$ is provided, said particles suspended in a fluid, the system comprising:
   a) a pixel array of detector elements having a pixel size p for simultaneously capturing one or more diffraction-enlarged images of the small particles formed upon the pixel array of the detector elements;
   b) imaging optics for forming images of the small particles on the pixel array, and for simultaneously causing a diffraction enlargement of the images to form the one or more diffraction-enlarged images; and,
   c) suitably programmed processing means for determining a pixel count per image for at least some of the one or more captured diffraction-enlarged images of the small particles, and for generating a number, size or distribution of particles, in dependence upon the diffraction-enlarged images;
wherein said diffraction enlargement of the images increases the pixel count per image by at least 5 pixels to a pixel count per image of at least N>5 pixels; and wherein said imaging optics has a linear magnification factor substantially smaller than $\text{sqrt}(N) \times d_{min}/p$.

In accordance with another aspect of this invention, a method of determining at least one of size, number and distribution of particles in a fluid comprising the steps of:
   a) providing a pixel array of detector elements to capture images of the particles exposed thereto;
   b) simultaneously enlarging images of a sample of particles by providing a diffraction enlargement system between the sample of particles and the pixel array of detector elements so that the images of particles from the sample of particles captured by the pixel array each occupy at least 5 more pixels than in the absence of said diffraction enlargement;
   c) capturing information from the pixel array corresponding to the sample of the diffraction enlarged images detected thereupon;
   d) and analyzing the information by probabilistically determining at least one of a number, size and distribution of the particles accounting for the diffraction enlargement.

BRIEF DESCRIPTION OF THE DRAWINGS

Exemplary embodiments of the invention will now be described in conjunction with the drawings in which.

DETAILED DESCRIPTION

The invention is a method and apparatus for measuring parameter distributions of small particles in flowing sample streams by forming diffraction-enlarged images of the particles on a pixel based detecting system and by making measurements on these images. The apparatus described in the invention utilizes an optical sampling volume which is much larger than that used in conventional microscopy. This is achieved by allowing particle images to contain a controlled and known degree of distortion. The system software corrects for this distortion and provides accurate measurements of parameter distribution.

Description of Exemplary Embodiments

Figure 1:
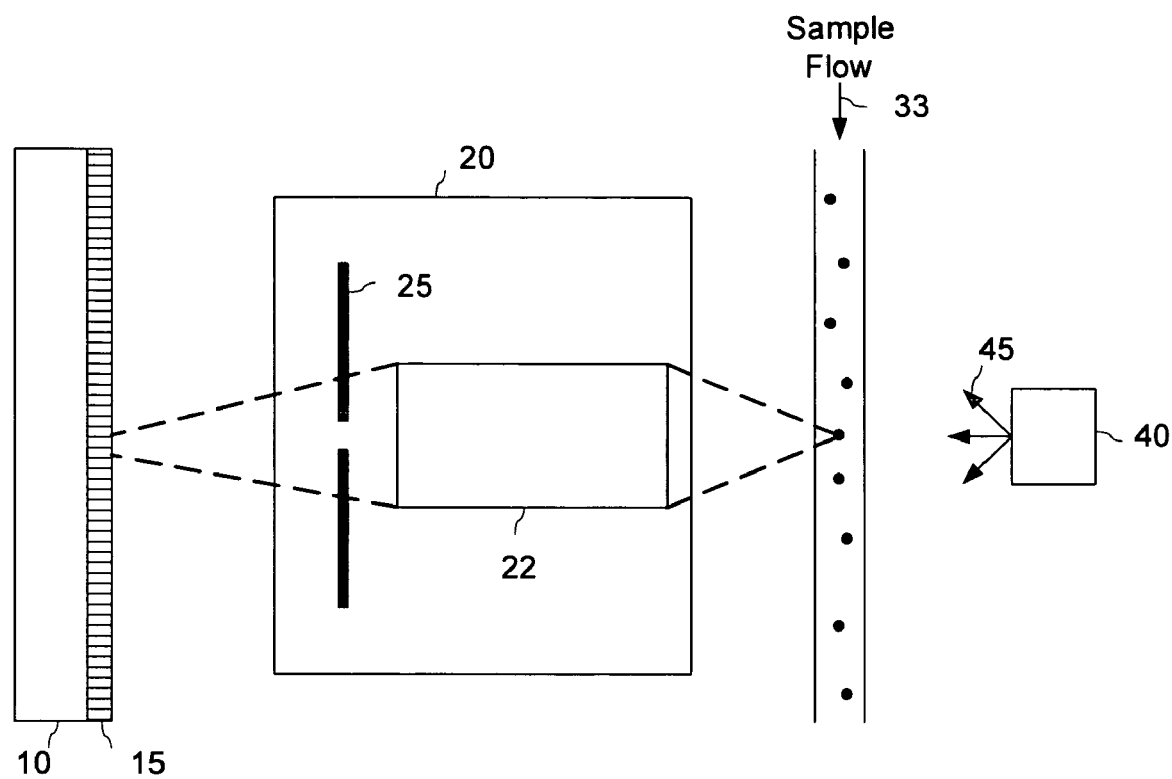
FIG. 1 is a diagram of the optical imaging system for measuring small particles using diffraction enlargement.

An exemplary embodiment of a system for measuring small particles in flowing sample streams by forming diffraction-enlarged digital images is shown in FIG. 1 and is hereafter described.

A CCD camera 10 is aligned to receive light from a light source 40 on a 2-D matrix of CCD detector elements 15; the 2-D matrix of CCD detector elements 15, which is a part of the CCD camera 10, is hereafter also referred to as a pixel array of detector elements. The light source 40 can be a lamp or a light-emitting diode. A transparent cell 30 containing a sample of liquid with small particles suspended therein is disposed in the path of the light between the CCD camera 10 and the light source 40. An objective lens system 22 such as a commercially available microscope objective is disposed between the cell 30 and the CCD camera 10 to collect at least a portion of the light passed through the transparent cell 30 and to focus it onto the CCD matrix 15. The portion of the light that the objective 22 collects is determined by its numerical aperture NA: a larger NA corresponds to a wider cone of light that the objective can collect. Normally in microscopy, imaging optics with a suitably large NA is used to suppress diffraction effects. By way of example, the second and third columns of Table 1 give magnification factors and NA values of several typical commercially available objectives. In contrast to the conventional approach, a diaphragm 25 having a numerical aperture $NA_2$ substantially smaller than NA is disposed adjacent to the objective 22 in the path of the light, to form an imaging optical system 20, hereinafter also referred to as imaging optics, having a substantially smaller NA than is typically used in conventional microscopy, as will be discussed hereinafter.

In operation, the light source emits light beam 45 illuminating a volume of the sample 33 inside the transparent cell 30. The objective 22 forms on the CCD array 15 an optical image of a portion of the sample of liquid 33 along with particles suspended therein. This portion of the sample is hereinafter referred to as an optical sampling volume v. Its optical image is captured by the CCD pixel array 15 which is used to convert the optical image into a digitized 2D image, hereinafter referred to as a frame, with each pixel representing an element of the frame of a size p, determined by a size and spacing of the detector elements of the CCD matrix.

The liquid sample 33 with particles typically flows through the transparent cell 30. Many successive frames, captured as the sample flows, are used to determine the particle parameter distributions and to capture selected images in statistically significant volumes of liquid. The parameter may be one of several possible parameters; for example cross-section, shape, or a particular bacteria, which corresponds to a predetermined cross-section range. For example bacteria B is known to be within a predetermined size range. Hence, detecting the numbers of bacteria B in a sample may be the desired goal.

Figure 2:
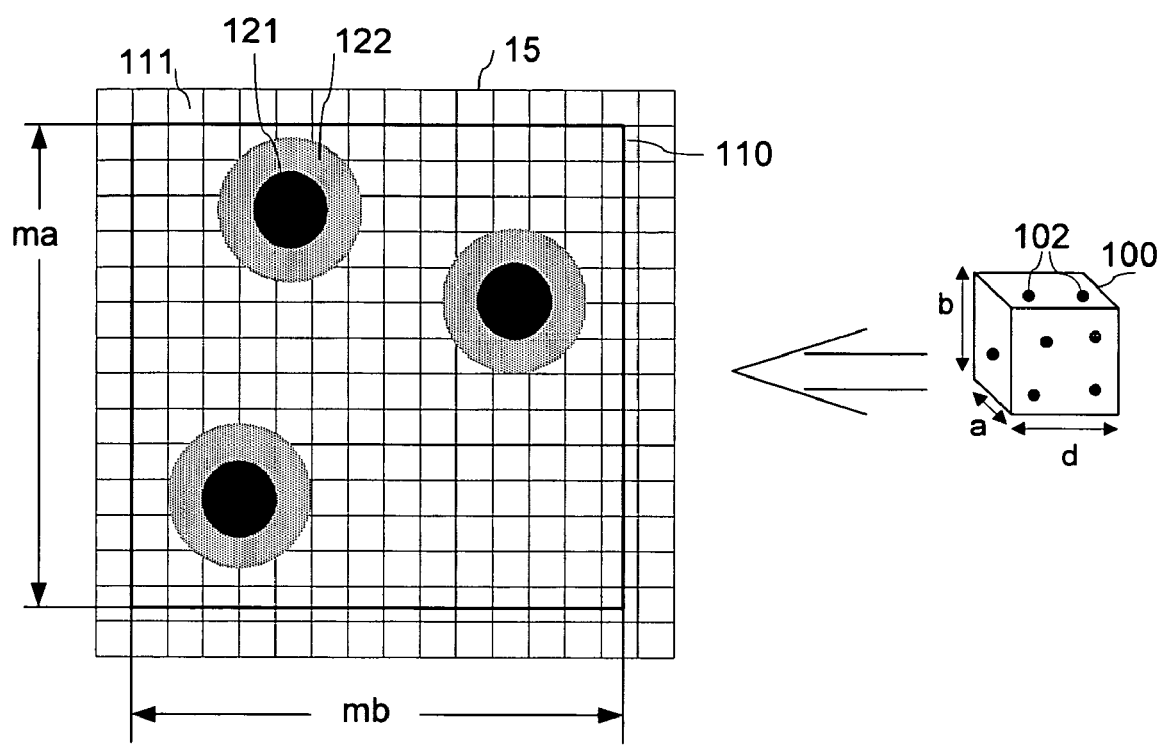
FIG. 2 is a diagram showing mapping of an optical sampling volume onto a 2D frame.

Similar to imaging in conventional microscopy, the imaging system shown in FIG. 1 maps an optical sampling volume v onto a 2D frame. This mapping is illustrated in FIG. 2 schematically showing the optical sampling volume 100 with particles 102 mapped onto a 2D optical image 110 formed upon the pixel array 15 formed by a rectangular matrix of detector elements 111. The optical sampling volume v labeled with a numeral 100 is determined by a field of view (FOV) a×b of the objective 22 and its depth of field (DOF) d, as marked in the FIG. 2: v=a×b×d; the objective 22 maps this sampling volume onto the 2D optical image 110 of a size m a×m b, where m is a magnification factor of the objective 22.

The 2D optical image 110 includes images of individual particles 102 from the optical sampling volume 100. In the embodiment shown in FIG. 1, images of individual particles are shadows of the particles imaged by the objective 22 onto the CCD detector array 15. In other embodiments light reflected from the particles can be collected by an imaging optics and projected onto a detector array. Electrical signals from each detector element, said electrical signals being dependent on the intensity of light to which a particular element is exposed to, are collected and compared to a pre-determined detection threshold, triggering either an "off" or "on" state of corresponding pixels of a digital 2D image. A cluster of adjacent "on" pixels is interpreted as a digital image of a particle, and a number N of pixels in the cluster is counted to determine a cross-section area of the image. This number of pixels in a digital image of a particle is referred to hereinafter as a pixel total or a pixel count per image.

Sufficiently accurate measurements on these images of individual particles require that each of them overlap and triggers at least a pre-determined minimum number $N_{min}$ of pixels of the pixel array. If an equivalent diameter of a smallest particle that has to be measured by the system is $d_p$, a corresponding particle image has to have an equivalent diameter $d_{im}$ of at least $(\sqrt{N_{min}}) \times p$, and the particle image has to be $k=(\sqrt{N_{min}}) \times p/d_p$ times larger than the particle. The equivalent diameter can for example be defined as the diameter of a circle having a cross-section area equal to the cross-section area of the particle. The factor k is hereafter in this specification referred to as a scaling factor or as an enlargement factor.

By way of example, the CCD camera has a pixel size of 7.5 μm, and $N_{min}=9$; minimum 9 pixels per image is often considered to be required for approximately 30% accuracy of measurement of an equivalent diameter of a particle. Each particle image has to have an equivalent diameter of at least 22.5 μm in this case. If 2 μm particles are to be measured, a scaling factor of 11.25 is required.

In some embodiments, it may be desirable that the smallest size particle to be measured triggers at least 15 pixels, $N_{min}=15$, for higher accuracy of individual measurements, requiring a scaling factor k=15.

As those skilled in the art would appreciate, normally there are at least two contributors to the total object-image enlargement factor k of an imaging and magnifying optics such as the microscope objective 22: the optical magnification and a diffraction enlargement. The optical magnification is substantially independent on the particle size, and provides a constant scaling factor m between an image size and a particle size. This conventional object-image magnification factor m, in the context of this specification the object being a particle, will be hereinafter also referred to as a linear magnification factor. The diffraction enlargement on the other hand depends on a size of the object, or a particle, e.g. on the effective diameter of the particle. This diffraction enlargement is caused by a finite aperture of the imaging optics and for a given m is typically inversely proportional to a square of the numerical aperture, i.e. $\sim 1/(NA)^2$.

In conventional microscopy, when an image of a small object such as a particle is being formed for purposes of measurement of a parameter of that object, an optical imaging system is used having a large optical magnification factor sufficient to allow measurements on the magnified image with a desired degree of accuracy. This is true whether the image is formed on a photograph and measured by eye using a graticule, or by pixel analysis of a digital image. Diffraction is typically regarded as a source of error as it leads to "smearing" of an image and reduces the system's resolution, which is defined as an ability of the magnification system to provide images in which closely spaced small objects do not overlap due to the diffraction enlargement and therefore can be differentiated. The diffraction enlargement is reduced by selecting a sufficiently large NA of the imaging optics so that the diffraction component is only a small fraction of the total object-image enlargement, for example less than 10% of the value of the parameter to be measured.

The conventional approach is therefore to select imaging optics having a magnification factor equal to the required enlargement factor, i.e. m=k, and also having a suitably large NA to suppress the diffraction enlargement. The scaling factor k used to convert an image size to a particle size is in this case largely independent on the particle size. However, the larger is the magnification, the smaller is the field of view (FOV) which determines the cross-sectional size of the optical sampling volume 100 as shown in FIG. 2. Furthermore, selecting a large NA typically leads to a small DOF, further decreasing the optical sampling volume. Table 1 gives examples of the FOV and DOF values for typical commercially-available objectives depending on their magnification and NA. The last column of Table 1 gives absolute values of diffraction enlargement (DE) in microns for the corresponding objectives, which are primarily determined by the NA.

TABLE 1

| Objective | Magnification | NA | FOV, mm² | DoF, µm | DE, µm |
|---|---|---|---|---|---|
| A | 2 | 0.055 | 3.3 × 4.4 | 91 | 5 |
| B | 5 | 0.14 | 1.3 × 1.7 | 14 | 2 |
| C | 10 | 0.28 | 0.66 × 0.88 | 3.5 | 1 |
| D | 100 | 0.7 | 0.07 × 0.09 | 0.6 | 0.4 |

By way of example, an objective "C" has a magnification factor 10 and NA=0.28. An image of a particle of a diameter $d_p$=2 µm formed with this objective will have a diameter $d_{im} \sim DE + m \times d_p = 21$ µm, and will occupy at least 9 pixels of size p=7.5 µm. It can be used to form an image of an optical sampling volume v as small as ~0.002 mm³

Contrary to the conventional approach, the method of the present invention is to use imaging optics having a small NA causing comparatively large diffraction enlargement of the smallest particles of interest, and a linear magnification factor m substantially smaller than a magnification factor that would have been required to image the same particles without the diffraction enlargement. The optical imaging system 20 therefore causes a comparatively large diffraction enlargement of images of small particles, and can also be referred to as a diffraction enlargement system.

Namely, the magnification factor m of the objective 22 is selected so that $$m < k = (\sqrt{N_{min}}) \times p/d_p \quad (1)$$

where $N_{min}$ is a minimum required number of pixels in an image, and $d_p$ is the equivalent diameter of a smallest particle of interest. NA is selected to provide, for the smallest particle of interest having the diameter $d_p$, a sufficient diffraction enlargement DE of its image to trigger with a high probability a pre-defined minimum pixels count $N_{min}$. IF $N_{min}$=9, condition (1) results in a requirement $$m < 3 \times p/d_p. \quad (1A)$$

By way of example, the system shown in FIG. 1 employs a CCD pixel array 15 with the pixel size p=7.5 µm, objective 22 of the type "B" from Table 1, i.e. the objective has a numerical aperture 0.14 and a magnification factor 5. If used alone, this objective provide a diffraction enlargement of less than 2 µm and a depth of field 14 µm. The diaphragm 25 has numerical aperture $NA_2 \ll NA_1$ sufficiently small to reduce the numerical aperture of the imaging system 22 to NA~0.03, yielding diffraction enlargement DE of ~10 µm. Table 2 shows the increase in a most probable pixel count by $n_d$ pixels which is obtained by adding the diaphragm 25 for this set of parameters, with $n_d$ ranging from 8 pixels for a 2 µm particle to 47 pixels for a 5 µm particle. Particles of 2 microns are seen to provide a most probable pixel count of 15 pixels. Particles this small would normally require linear magnification of approximately ×10 in a conventional system to provide an equivalent number of pixels. The ×5 system with the reduced NA has an optical sampling volume which is approximately 40 times larger than the ×10 conventional system.

TABLE 2

| Particle size, µm | Pixel count w/o diff. enlargement | Pixel count with diff. enlargement |
|---|---|---|
| 2 | 7 | 15 |
| 3 | 12 | 47 |
| 4 | 16 | 55 |
| 5 | 23 | 70 |

The effect of the diaphragm 25 is further illustrated in FIG. 2 showing images of 3 small articles. Without the diaphragm 25, the three images formed upon the pixel array 15 by the objective 22 are shown by dark circles 121, overlapping less than 9 pixels. With the NA-reduced system of FIG. 1 including the diaphragm 25, the images have a diffraction-induced halo 122, or a fringe pattern of reducing intensity extending beyond the circles 121, and are thereby diffraction-enlarged to occupy more than 9 pixels. A diffraction enlargement by at least $n_d$=5 pixels per each image is required to noticeably decrease either the minimum measurable particle size, or the pixelation error for the small particles of same size. In relative terms, the diffraction enlargement should be at least 30% of the minimum pixel count per image, or $n_d > N_{min}/3$, and preferable 100% or more than $N_{min}$.

The diffraction enlargement results in a distorted image of the particle, which would not be acceptable in the conventional microscopy imaging. However, since the distortion is measurable and consistent, its contribution can be removed during processing of the image data using appropriately programmed processing means, such as a computer, a DSP, and FPGA or a similar processing module as would be obvious to those skilled in the art; the processing means is hereinafter referred to as simply a processor. The processor includes memory having a plurality of scaling coefficients stored therein, preferably embodied as a look-up table. The scaling coefficients relate the particle size such as an equivalent diameter to a pixel count in order to accurately determine the particle parameters. The processor receives pixel state information from the pixel array 15, and using appropriate software determines which pixels form images of particles, generates pixel count per image, and uses the look-up table to determine a number, size or distribution of the particles, in dependence upon the images captured by the detector array 15.

The contribution of the dispersion enlargement has however first to be detected and converted into the increased pixel total; for this purpose the system of this invention employs a highly sensitive pixel detection threshold so that the diffraction component in the images are included in the image measurements. This is contrary to a setting of the pixel detection threshold in conventional microscopy employing detector arrays, which typically has the threshold set so to exclude the diffraction effect on the image.

Although the system of present invention can operate either in a brightfield mode when light passes through the sample, or a darkfield mode when light is reflected or scattered backwards from the sample, the brightfield mode shown in FIG. 1 is preferred. In this mode, particles images are darker than the bright background. In the absence of any light, each detector element, or a pixel, generates a small noise signal output. Signal output from each pixel saturates if the pixel receives an amount of light above a certain level. A working range of a pixel is a range between the noise level and the level where this saturation effect starts to become significant. By way of example, each pixel outputs a 10 bit signal output in response to received light, i.e. 1023 signal levels wherein 1023 is the maximum signal level. The illumination light 45 is adjusted to provide a background level of the pixel signal output of 900. The pixel detection threshold, i.e. a level at which the system software decides that a pixel is a part of a particle image, is set as close as possible to this maximum level of 900 in order to detect the smallest possible change in intensity due to the presence of a particle and to pick up the diffraction enlargement region, i.e. the diffraction halos shown in FIG. 2, but far enough from the background level to exclude the noise contribution which can cause pixels to be incorrectly counted. By way of example, a threshold of 96.4% of the background level is set in one embodiment. This compares with a threshold of about 75% which might be employed in a conventional setup which depends on linear magnification and where diffraction is regarded as a source of error. Still more sensitive pixel detection threshold can be used in other embodiments providing a stronger noise reduction, e.g. by using a cooled pixel array or other means.

The scaling coefficients stored in the lookup table include values of diffraction enlargement, which can be either measured or calculated, for different particle parameter values. As a way of example, the scaling coefficients are measured using a following procedure. First, samples containing calibration particles of known diameters are examined using a given system configuration, i.e. the numerical aperture, magnification setting, diaphragm setting, sample flow depth, etc. Results of the measurements in a form of measured pixel count distribution, i.e. frequency of occurrence of a particular pixel count, are converted to image diameters using the method disclosed in U.S. patent application Ser. No. 10/653, 133 by a same inventor as the current invention, which is incorporated herein by reference. The overall effective enlargement containing contributions from both the diffraction and the optical magnification is determined for each particle size. These results are used to prepare the look-up table which is then used to calculate particle size data from image size data on real samples.

Summarizing, the system employs magnification optics with a lower numerical aperture, preferably less than 0.06, and a lower magnification compared to those normally required to obtain satisfactory images of small particles using conventional microscopy. The low NA provides an increased depth of focus, since the depth of focus of an optical system is proportional to $1/NA^2$. However the low numerical aperture also results in enlargement of the particle images as a result of diffraction, this diffraction enlargement is known to be inversely proportional to the numerical aperture of the system. Because of this diffraction enlargement, the magnification value used by the system is reduced while still obtaining an image which is sufficiently large to occupy an acceptable number of pixels for the smallest particles of interest.

The diffraction enlargement results in a distorted image of the particle normally considered undesirable or even unacceptable in conventional microscopy imaging. However, since the distortion is measurable and consistent, in the system and method of this invention its contribution is removed in the processing software in order to accurately determine the particle parameters. Using this technique at a magnification value of times 4.5, a 1.5 micron diameter particle forms an image on the pixel array having a diameter of approximately 23 microns through the combination of magnification and diffraction. This is sufficient for a diameter measurement accuracy of approximately 30%. With these settings, a depth of focus of 0.5 mm and a field of view of 2×2 mm may be employed. Using these settings the optical sampling volume is increased by a factor of approximately 3000 compared with that using conventional microscopy.

In other embodiments, the optical sampling volume is further increased by increasing the depth of the sample to point where part of the particle population is located sufficiently far from the focal plane that they become partially out-of-focus. This out-of-focus enlargement is modeled based on a measured particle distribution in the sample volume and on measurements of this out-of-focus enlargement at different distances from the focal plane. This model is then applied to correct, for a sample of particles of interest, a measured distribution of particle diameters to remove the out-of-focus distortion and obtain correct diameter distribution data.

The aforedescribed embodiment shown in FIG. 1 employs the microscope objective 22 having the low magnification and the high NA, and uses the diaphragm 15 to substantially decrease the effective NA of the imaging optics 20 formed thereby. This arrangement allows the use of commercially widely available and therefore relatively inexpensive objectives typically having high values of NA>0.1. In other embodiments, an objective lens system having the desired low NA, preferably less than 0.05, and the desired magnification factor can be used instead as the imaging optics 20 without the use of the diaphragm.

Of course numerous other embodiments may be envisioned without departing from the spirit and scope of the invention.

What is claimed is:

1. A system for measuring small particles suspended in a fluid, comprising:
   a pixel array of detector elements for simultaneously detecting one or more images of the particles formed thereupon;
   an imaging system for forming the images of the particles on the pixel array, said imaging system comprising imaging optics for causing a diffraction enlargement of each of the images by at least $n_d$ pixels each thereby providing diffraction-enlarged images, said at least $n_d$ pixels in operation capturing a diffraction-induced component of each diffraction-enlarged image, wherein $n_d$ is equal to 5, for reducing a pixelation error; and, suitably programmed processing means for determining at least a pixel count for each of the diffraction-enlarged images, and for generating a number, size or distribution of particles, in dependence upon the diffraction-enlarged images captured by said imaging system.

2. A system of claim 1 wherein the imaging optics has a numerical aperture NA selected to provide the diffraction enlargement of the images.

3. A system of claim 2 having a minimum pixel count per image $n_{min}>1$ for image detection, wherein $n_d$ is greater than $n_{min}/3$.

4. A system of claim 3 wherein said minimum pixel count corresponds to a minimum particle diameter $d_{min}$ less than 3 µm.

5. A system of claim 4 having a pixel size p µm, wherein the imaging optics has a linear magnification factor m less than $3 \times p/d_{min}$.

6. A system of claim 3 wherein $n_{min}$ is at least 15.

7. A system of claim 3 wherein $n_{min}$ is at least 9.

8. A system of claim 1 having a pixel detection threshold set at a level suitable for detection of the diffraction-induced component of the images.

9. A system of claim 1 wherein the processing means adapted for calculating a particle size for a plurality of particles in a sample in the presence of diffraction enlargement.

10. A system of claim 9 wherein the processing means includes memory having a plurality of scaling coefficients stored therein, said scaling coefficients relating the particle size to a pixel count.

11. A system of claim 5 wherein the imaging optics comprises an objective lens system having the magnification factor m and the numerical aperture NA.

12. A system of claim 5 wherein the imaging optics comprises:
   an objective lens system having the magnification factor m and a numerical aperture $NA_1$, greater than NA;
   a diaphragm disposed between the objective lens system and one of the fluid and the pixel array, the diaphragm having a numerical aperture $NA_2$ substantially smaller than $NA_1$ for increasing the diffraction enlargement of the images and a depth of focus of the imaging optics.

13. A system for measuring a sample of small particles wherein at least some of the particles are at least as small as 2 µm, said system comprising:
   a pixel array of detector elements for detecting one or more images of the small particles formed thereupon;
   an imaging system for forming the images of the small particles on the pixel array of detector elements, said imaging system comprising:
   a) a source of light for illuminating the particles,
   b) an objective lens system for forming the images upon the pixel array of detector elements, the objective lens system having a magnification of less than 6 and a numerical aperture less than 0.05;
   suitably programmed processing means for generating at least a pixel count per image, and for determining a number, size or distribution of the particles, in dependence upon the images captured by said imaging system.

14. A system for measuring small particles having a diameter $d_{min}$, said particles suspended in a fluid, the system comprising:
   a pixel array of detector elements having a pixel size p for simultaneously capturing one or more diffraction-enlarged images of the small particles formed thereupon;
   imaging optics for forming images of the small particles on the pixel array, and for simultaneously causing a diffraction enlargement of the images to form the one or more diffraction-enlarged images; and,
   suitably programmed processing means for determining a pixel count per image for at least some of the one or more captured diffraction-enlarged images of the small particles, and for generating a number, size or distribution of particles, in dependence upon the diffraction-enlarged images;
   wherein said diffraction enlargement of the images increases the pixel count per image by at least 5 pixels to a pixel count per image of at least N>5 pixels; and wherein said imaging optics has a linear magnification factor substantially smaller than $\sqrt{N} \times d_{min}/P$.

15. A method of determining at least one of size, number and distribution of particles in a fluid comprising the steps of:
   providing a pixel array of detector elements to capture images of the particles exposed thereto;
   simultaneously enlarging images of a sample of particles by providing a diffraction enlargement system between the sample of particles and the pixel array of detector elements so that the images of the sample of particles captured by the pixel array each occupy at least 5 more pixels than in the absence of said diffraction enlargement;
   capturing information from the pixel array corresponding to the sample of the diffraction enlarged images detected thereupon;
   and analyzing the information by probabilistically determining at least one of a number, size and distribution of the particles accounting for the diffraction enlargement.

* * * * *